(12) United States Patent
Hickey et al.

(10) Patent No.: US 7,857,272 B1
(45) Date of Patent: Dec. 28, 2010

(54) HOLDER FOR ARM-MOUNTED MEDICAL IMAGING PROBE

(75) Inventors: Katherine M. Hickey, Enfield, NH (US); Aaron M. Gjerde, Lebanon, NH (US); James H. Bleck, Chelmsford, MA (US); Leslie Scenna, Amherst, NH (US)

(73) Assignee: Wellan Medical Solutions, LLC, Lebanon, NH (US)

( * ) Notice: Subject to any disclaimer, the term of this patent is extended or adjusted under 35 U.S.C. 154(b) by 520 days.

(21) Appl. No.: 11/870,019

(22) Filed: Oct. 10, 2007

Related U.S. Application Data

(60) Provisional application No. 60/851,351, filed on Oct. 12, 2006.

(51) Int. Cl.
*E04G 3/00* (2006.01)

(52) U.S. Cl. .................................... 248/288.31

(58) Field of Classification Search ................. 600/407, 600/459; 248/229.26, 228.7, 230.7, 231.81, 248/288.31, 274.1; 73/866.5
See application file for complete search history.

(56) References Cited

U.S. PATENT DOCUMENTS

| | | | | |
|---|---|---|---|---|
| 4,282,783 A | * | 8/1981 | Fortune ..................... | 81/427.5 |
| 6,357,710 B1 | * | 3/2002 | Fielden et al. ............ | 248/276.1 |
| 6,793,664 B2 | * | 9/2004 | Mazzocchi et al. .......... | 606/157 |
| 7,547,110 B2 | * | 6/2009 | Vaught ....................... | 362/123 |
| 2008/0317096 A1 | * | 12/2008 | Hsieh ......................... | 374/158 |

* cited by examiner

*Primary Examiner*—Terrell Mckinnon
*Assistant Examiner*—Erin Smith
(74) *Attorney, Agent, or Firm*—William A. Loginov, Esq.; Loginov & Associates, PLLC

(57) ABSTRACT

This invention provides a holder for an imaging probe that attaches to a flexible arm, which accommodates a variety of sizes and shapes of probes, is lightweight and allows for easy attachment and detachment of probes. The probe holder includes a pair of confronting clamp plates that include clamping jaws for holding a probe or other item at their distal end. The distal ends of the plates can include elastomeric pads that conform to the shape of the probe being gripped. The proximal end of each plate includes a hemispherical well that engages a ball on a base member to define a highly flexible ball joint. This ball joint allows for easy fine adjustment of probe alignment, rotation and tilting, while frictionally maintaining the set position. A variety of alternate alignment and movement-limiting components can be employed.

12 Claims, 16 Drawing Sheets

HOLDER FOR ARM-MOUNTED MEDICAL IMAGING PROBE

RELATED APPLICATION

This application claims the benefit of U.S. Provisional Application No. 60/851,351, entitled HOLDER FOR ARM-MOUNTED MEDICAL IMAGING PROBE, by Katherine M. Hickey, et al., filed Oct. 12, 2006, the teachings of which are expressly incorporated herein by reference.

BACKGROUND OF THE INVENTION

1. Field of the Invention

The invention relates to medical devices and, in particular, to a device for positioning and stabilizing diagnostic or therapeutic devices used in medical procedures.

2. Background Information

In clinical practice, there are many different procedures utilized for various diagnostic, therapeutic, monitoring, or guidance applications. These are typically conducted by a highly skilled operator who relies heavily on the ability to simultaneously perform multiple tasks, such as viewing a monitor while positioning a probe or dissecting tissue while exerting separation force upon the walls of an incision. Examples of such medical tasks include, but are not limited to, invasive radiology (for breast biopsy), local anesthesia (for peripheral nerve blocks), invasive cardiology (for stent placement and deployment), vascular surgery (for measuring intravascular blood flow), and general surgery (for retraction of the incision walls or holding a hemostat clamping device).

By way of example, peripheral nerve blocks are used by anesthesiologists and pain doctors to anesthetize nerves that are involved in the transmission of pain signals during surgery or states of chronic disease. The image-acquisition procedure requires at least one of the operator's hands to be continually occupied at a high level of concentration and dexterity for probe manipulation. In general, the practitioner must carefully orient the probe and maintain it in relative contact with the anatomical region to acquire a good image. A second skilled operator must be employed to insert the needle, then deliver the required drug; undoubtedly a task requiring two hands.

Peripheral nerve blocks fall under the category of regional anesthesia, which indicates only a portion of the body is anesthetized and/or desensitized. This is in contrast to general anesthesia, in which the patient is placed into a state of complete unconsciousness. Nerve blocks entail the deposition of local anesthetics, such as lidocaine, which block the transmission of the pain signals for a variable amount of time. The major challenge for the clinician performing nerve blocks is related to finding the nerve of interest. Traditional anesthesiology approaches rely on palpating external landmarks on the skin, assuming that the anatomy below is normal, and subsequently inserting a needle attached to a nerve stimulator. When the needle contacts the nerve, a twitch occurs in the muscle that is interconnected with the nerve. By this method, the practitioner knows where to inject.

Because anatomy is variable, this technique results in significant failure rates, multiple needle passes, and significant potential for pain and injury to the nerve and adjacent structures. Modern ultrasound technologies allow the operator to guide his or her needle under live visualization to the structures of interest. The operator can then avoid multiple needle sticks, avoid structures (such as blood vessels), and confirm that the local anesthetic is spreading around the nerve of interest. However, current ultrasound approaches to performing nerve blocks and any other procedures (placement of intravenous catheters, breast biopsies, etc.) require that the operator hold the ultrasound probe in at least one hand in engagement with the anatomical region of interest. Once a satisfactory image of the structure is acquired, subtle movements of the hand holding the probe may result in degradation of the image, requiring a repositioning of the probe.

In addition to anatomical differences between patients, traditional landmark and nerve stimulator techniques can produce incomplete blockage of pain for patients because the drugs administered may not completely perfuse the nerves. Ultrasound not only enables the practitioner to visualize the target nerves and needle, but also the drugs deployed. If necessary he/she can reposition the needle and deploy drugs to the unblocked portions, ensuring a complete blockage of pain.

The pressure applied to the region of interest/treatment by the procedure guiding probe is critical. Too much pressure tends to distort the underlying tissues, making for an inaccurate image and pinching of internal tissues that may lead to misdirection of the needle. Too little pressure yields a bad image. During the procedure, the guiding probe is employed previous to needle insertion. Hence, the practitioner generally uses the "strong" hand (e.g. the right hand for a right-handed person) to guide and position the probe. This leaves the task of needle insertion either to the practitioner's weak hand or a second practitioner. The single-practitioner approach is rarely used in practice, both due to quality and safety concerns and also to prevailing medical practice rules and custom. Hence, two practitioners are, in fact, employed to perform the procedure (e.g. block, placement of intravenous catheters, breast biopsies). The second practitioner is needed to hold the probe, as the primary operator administers therapy—a task encompassing the injection of medicine, placement of the catheter, or performing the biopsy.

A solution to the problem of "too few hands" is taught in copending U.S. patent application Ser. No. 11/338,270, entitled BIOMEDICAL POSITIONING AND STABILIZATION SYSTEM by Katherine M. Hickey, et al., the teachings of which are expressly incorporated herein by reference. This teaching provides a flexible stand that includes a flexible arm constructed from a plurality of polymer segments that are selectively connected by a ball-and-socket system. The segments can be locked into position or held by friction alone. The stand 100 is shown in detail in FIG. 1. In one arrangement, it consists of an upright post 102 that rests on the ground that supports the proximal end 108 of the flexible arm 104. Note that the arm segments are covered by a sterile sheet 106. Alternatively, the flexible arm can be supported from a ceiling or wall mount, a cart or an imaging device housing, among other surfaces. The arm's distal end 110 carries a mounting bracket 112 that engages a medical ultrasound probe in this example. The probe is held firmly using clamps, friction, set screws or another mechanism. In use, the practitioner 116 manipulates the flexible arm, mounting and probe into an appropriate orientation against the patient 120, and then fine tunes the probe's position with respect to the target area on the patient to obtain the desired image, which is transmitted via a cable 130 to an imaging device (not shown). Either the inherent friction generated between arm segments or a positive locking mechanism holds the probe stationary against the target area, allowing the practitioner 116 to use both hands to administer appropriate treatment via needles and the like, while observing the path of the needle into the patient's body on the display.

The task of manipulating the probe into the optimum position for imaging the target involves moving the mounting/ probe in several degrees of freedom. Referring to FIGS. 2-4, a prior art freehand, probe-manipulation technique is shown and described. In FIG. 2, the practitioner's hand 200 manipulates the probe 210 to establish an appropriate lateral alignment, using a side-to-side motion (arrows 220). This positions the probe at the appropriate point on the patient's body.

Once the general location has been established, the practitioner's hand 200 rotates (arrows 300) the probe 210 with respect to the target area so that it is oriented to properly face the region being imaged. The practitioner may consult the display of the imaging device to establish the proper rotational orientation. The display should provide an image that is, in essence, "right-side-up" with respect to the practitioner's point of view. Rotation will establish the appropriate orientation, and also produce the best image of the target area.

The next adjustment is tilt, which is shown in FIG. 4. In general, the practitioner's hand 200 must tilt (arrows 400) the probe 210 so that its face is generally orthogonal to the target surface. If the probe's face is skewed to the target surface, the image will be inferior or unreadable. This orientation, like alignment and rotation, is established based upon feedback from the viewed imager display.

The order of adjustments as described above can be varied and they can be carried out simultaneously.

The required adjustment of the probe in alignment, rotation and tilt can be labored using a relatively fixed holder on the above-described flexible arm. While the arm structure is technically capable of movement in each of the desired degrees of freedom, the segments tend to drag against each other frictionally when the arm is biased in a direction. This creates a situation where the practitioner tends to overshoot the desired target location. Thus, in practice, using the arm to manipulate each of alignment, rotation and tilt can prove laborious and inaccurate.

Thus, it is desirable to provide a more localized mechanism on a flexible arm, adjacent to a practitioner's hand, for manipulating the alignment, rotation and tilt of held probe. It is also desirable to provide a probe holder that effectively and firmly grasps a variety of probe sizes and form factors and that allows easy attachment and detachment of the probe from the holder.

SUMMARY OF THE INVENTION

This invention overcomes the disadvantages of the prior art by providing a holder for an imaging probe that attaches to a flexible arm, which accommodates a variety of sizes and shapes of probes, is lightweight and allows for easy attachment and detachment of probes. The holder has a pleasing and ergonomic shape and accommodates a variety of gripping surfaces that can include customized decorations and/or sculpting. In an illustrative embodiment, the probe holder includes a pair of confronting clamp plates that include clamping jaws for holding a probe or other item at their distal end. The distal ends of the plates can include elastomeric pads that conform to the shape of the probe being griped. The proximal end of each plate includes a hemispherical well that engages a ball on a base member to define a highly flexible ball joint. This ball joint allows for easy fine adjustment of probe alignment, rotation and tilting, while frictionally maintaining the set position. The base member is attached to a flexible arm that can be constructed from a plurality of hollow, ball-and-socket segments. The plates are biased toward each other, and toward the ball joint by one or more elastic bands that surround the exterior of the plates near their proximal ends generally ahead of the diametral axis of the ball. The plates are aligned against skew using a T-shaped member that engages a conforming slot on each plate interior surface. A variety of alternate alignment and movement-limiting components can be employed. The T-shaped member also acts to provide a proximal backstop to the further proximal movement of the probe, helping to ensure that its head remains exposed for engagement with a target area on a body.

The probe holder can include an undercut surface to accommodate removable gripping surfaces that can include logos or ergonomic sculpting that facilitates positive grip by a user. The geometry of the ball, bands and plates allows the plates to expand to accommodate probes of differing sizes and thicknesses. The thicker (and more weighty) the probe, the greater the pressure bearing upon the ball by the wells based upon leverage. This aids in applying proportionally greater holding friction to the ball that assists in maintaining the set position of a heavier probe.

The plates can be limited in movement toward and away from each other so that the jaws remain open when in a resting state (without attached probe), but at a spacing that is smaller than the minimum expected probe thickness. In this manner, the probe may be inserted, one-handed, into the holder by a practitioner. This further enhances the hands-free nature of the holder and underlying flexible arm.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
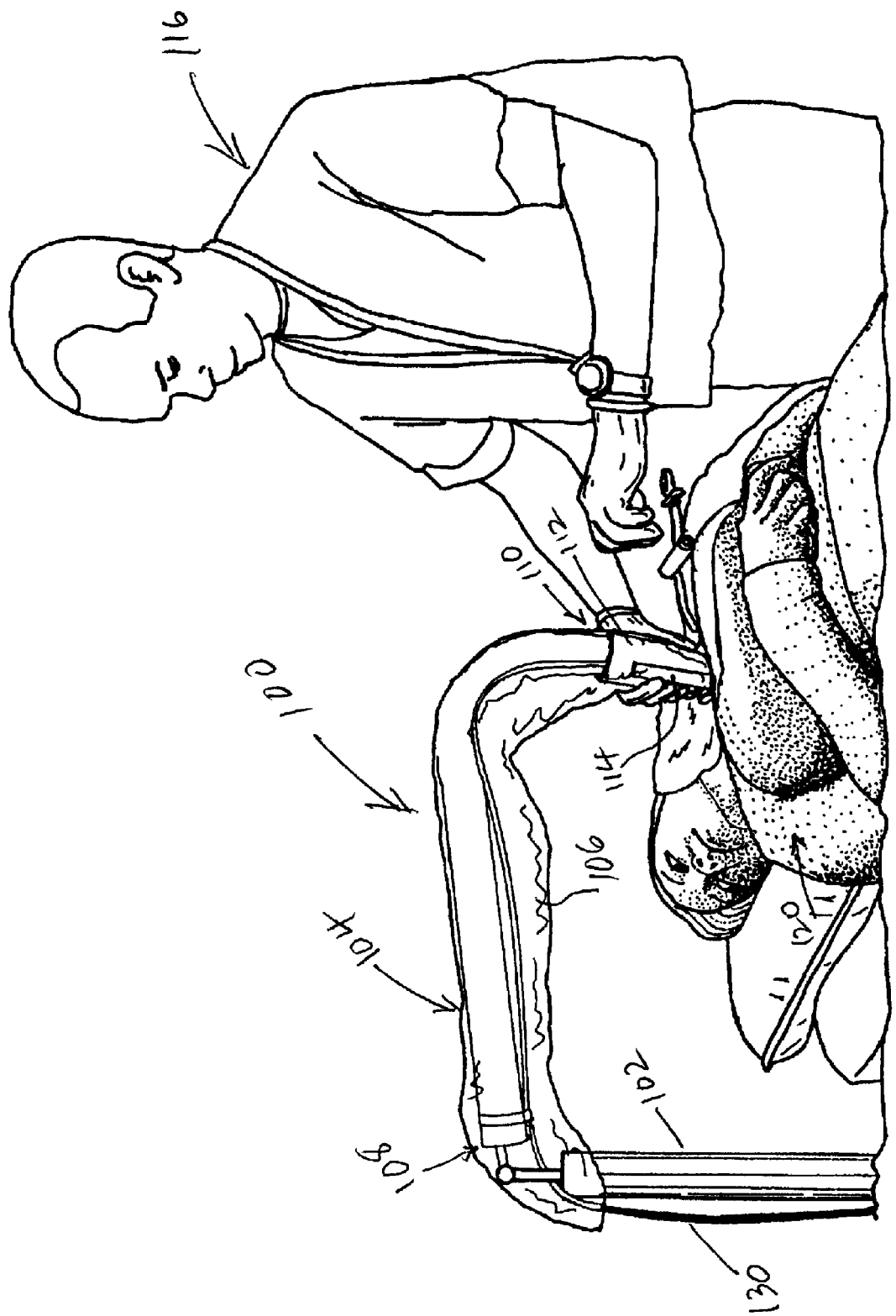
FIG. 1, already described, is a perspective view of a typical imaging procedure employing a probe-holding holder and stand-mounted flexible arm.
Figure 2:
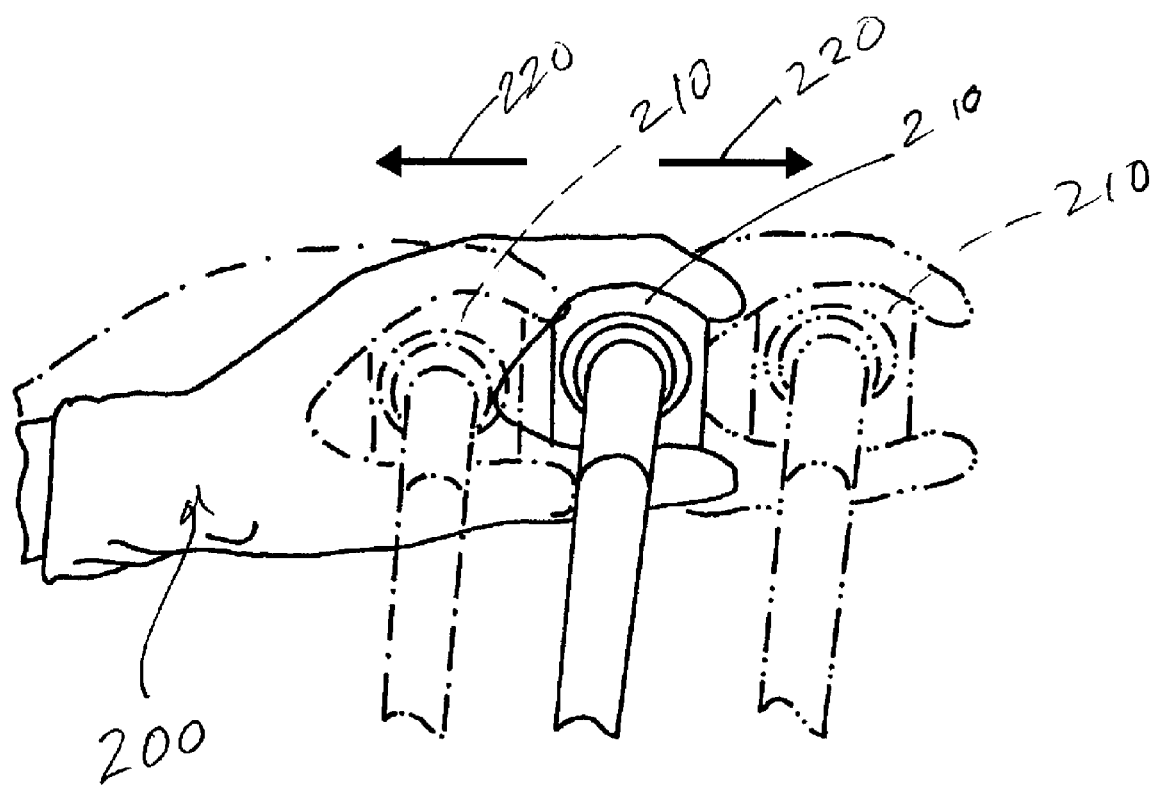
FIG. 2, already described, is a fragmentary top view of a practitioner's hand manipulating a freehand imaging probe to establish desired alignment on a target surface.
Figure 3:
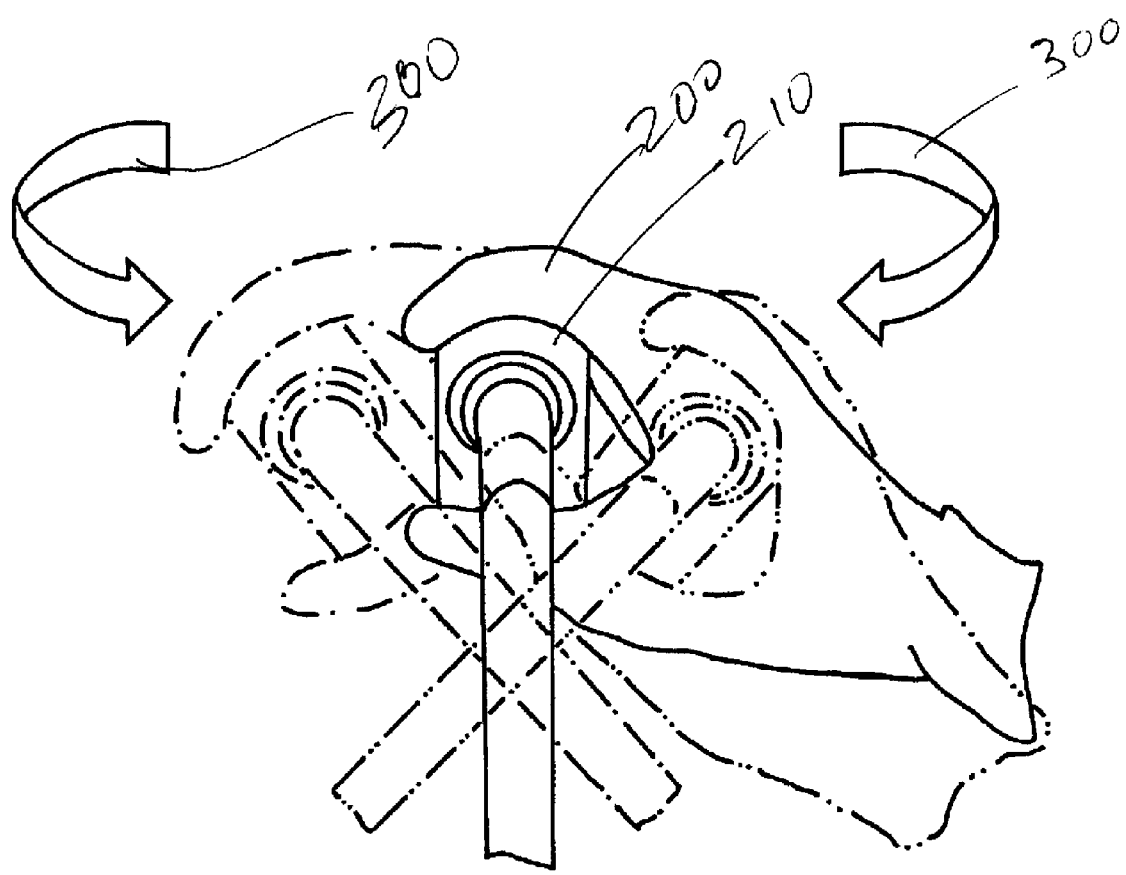
FIG. 3, already described, is a fragmentary top view of a practitioner's hand manipulating a freehand imaging probe to establish desired rotation on the target surface.
Figure 4:
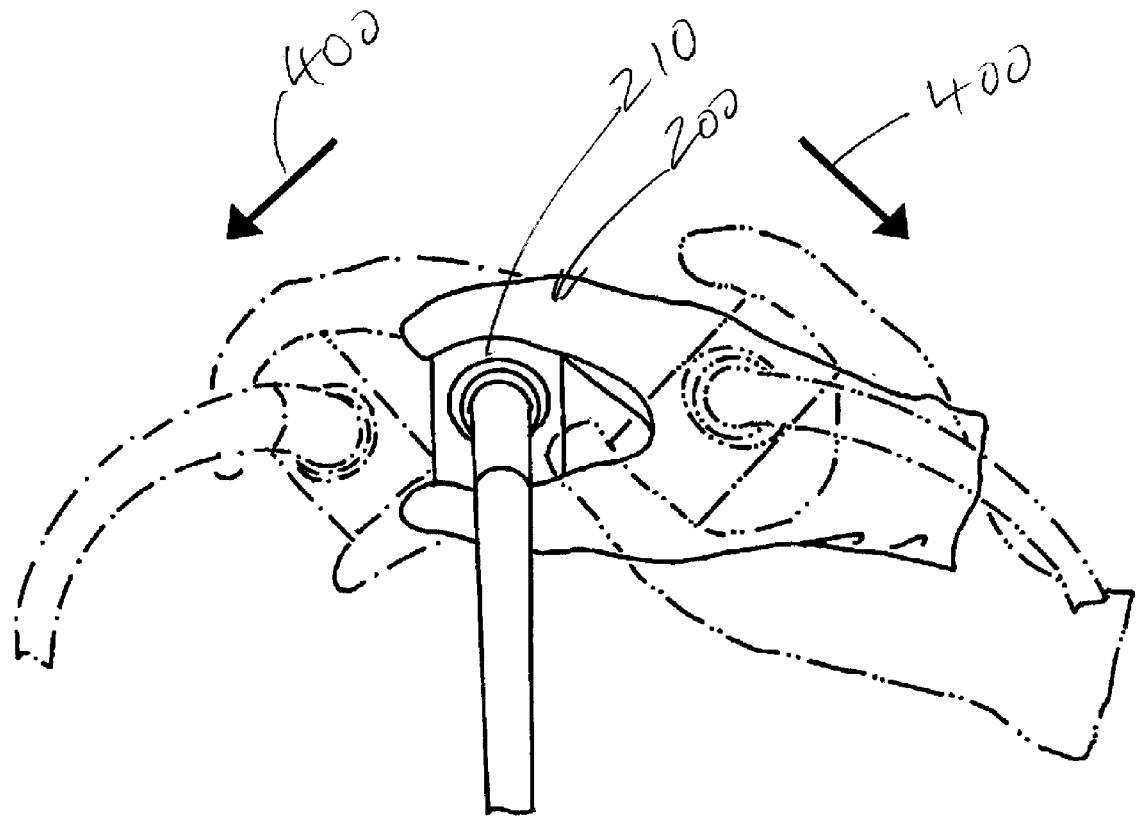
FIG. 4, already described, is a fragmentary top view of a practitioner's hand manipulating a freehand imaging probe to establish desired tilt on the target surface.
Figure 5:
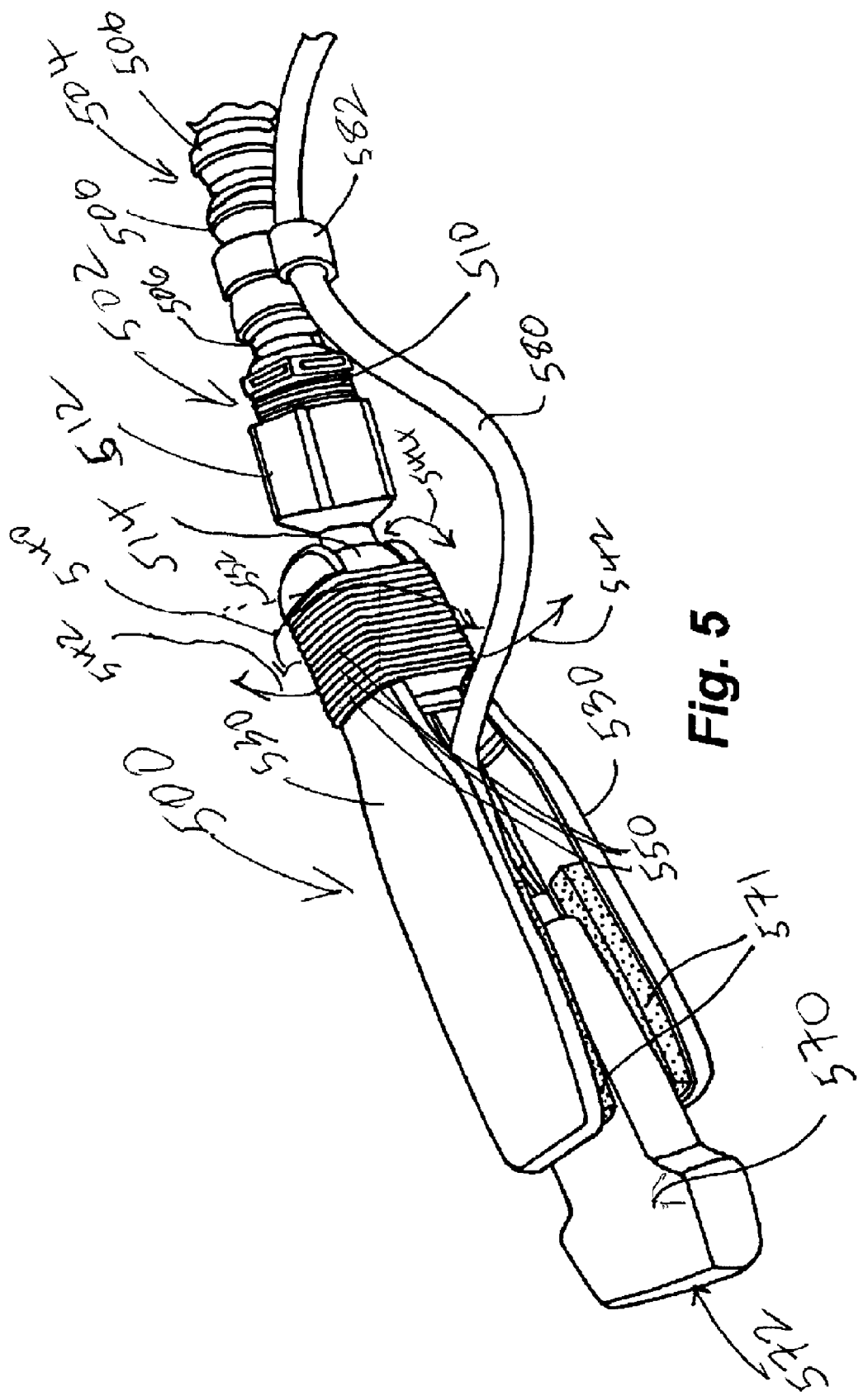
FIG. 5 is a perspective view of the probe holder according to an illustrative embodiment attached to a flexible, segmented arm in accordance with an embodiment of this invention.
Figure 6:
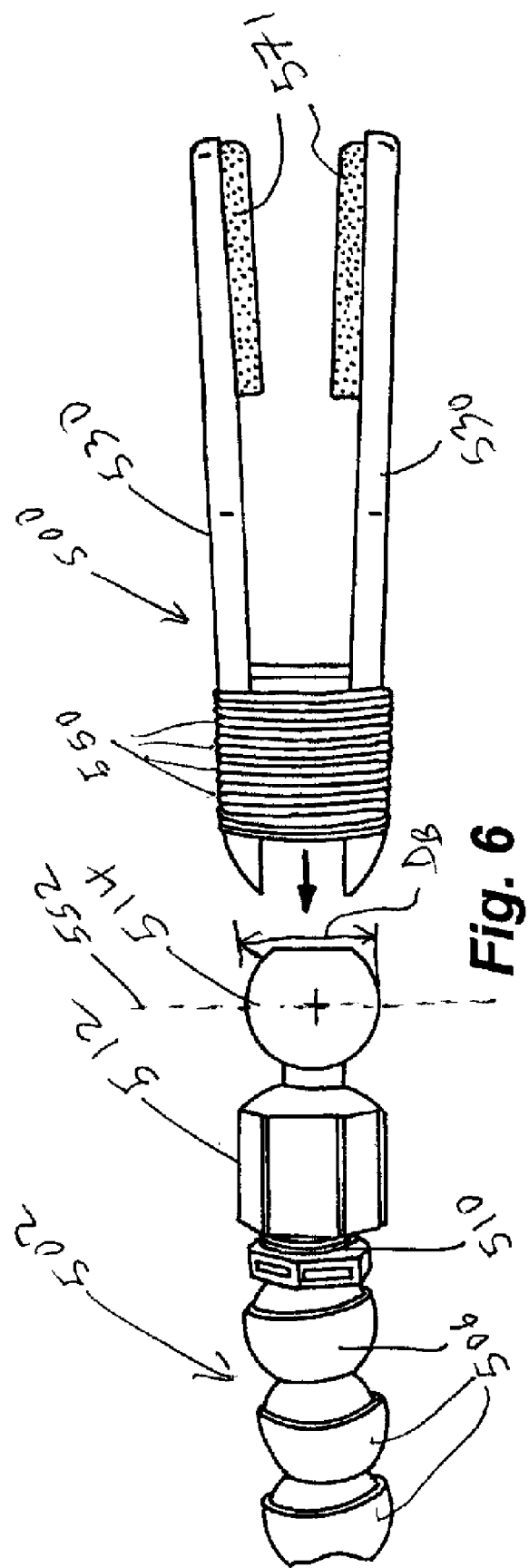
FIG. 6 is an exploded side view of the probe holder of FIG. 5.

FIGS. 5 and 6, detail a probe mount 500 in accordance with an illustrative embodiment of this invention. The mount 500 is attached to the distal end 502 of a flexible arm 504 that is constructed from a series of interconnected, plastic segments 506 typically in accordance with the above-incorporated U.S. patent application Ser. No. 11/338,270, entitled BIOMEDICAL POSITIONING AND STABILIZATION SYSTEM. Alternatively, attachment of the probe mount to any type of flexible, semi-flexible or swiveling arm is expressly contemplated. The distal end 502 of the arm 504 includes a threaded end 510, which includes a male thread in this embodiment. The end 510 engages a female base 512 at the proximal end of the probe holder 500. The base 512 is constructed from polymer for strength and lightness of weight. The base includes a ball end 514, which is described further below. Briefly, the ball 514 engages a pair of holder clamp plates 530 that are identical or similar in this embodiment. These plates can swivel on the ball in at least three degrees of freedom, arbitrarily termed "roll" (curved arrow 540), "pitch" (curved arrows 542) and "yaw" (curved arrow 544). The plates 530 are removably secured to the ball 514 using one or more elastic bands 550 that can be constructed from rubber, polyurethane, polyisoprene, or another suitable elastomer. The bands 550 are mounted, for the most part, distally of the balls diametral axis so that the bands force the distal ends of each plate 530 together while maintaining pressurable contact between the plates 530 and the ball 514. This pressurable contact exerts low, but sufficient holding friction between the plates and the ball so that the holder can be easily swiveled, and thereafter maintain its position. Note that, in this description, "diametral axis" means an axis as shown, which extends vertically through the ball orthogonal to a proximal-to-distal and widthwise direction.

The plates 530 include an elastomeric material 571 along their confronting, distal inner surfaces that frictionally engages an exemplary probe 570 (see FIG. 5). The probe is held firmly in the clamped position with its scanning head exposed for engagement with a target area on a body. The material used for the gripping members 571 is highly variable. The list of possible elastomers includes, but is not limited to, neoprene foam, polyurethane, polyolefin, polyisoprene, gel bladders, and various other low-durometer plastics.

The force of the bands 550, combined with the frictional characteristics of the material ensure a firm grip for the probe. The degree of gripping force can be varied by increasing the number/surface contact, thickness, durometer and material of the bands 550. The probe includes a power and data cable 580 in this example. Wireless probes are contemplated in alternate embodiments. The cable 580 extends out of the probe holder 500, and thereafter along the arm 502. A novel clip is provided at one or more locations along the arm 502 to secure the cable, and prevent it from dangling in an interfering manner.

The probe holder 500 of this invention can accommodate a wide range of ultrasound and similarly sized and shaped tools. The illustrated probe is an L38e made by SonoSite, Inc. in Bothell, Wash. A range of probes from SonoSite, in both its MicroMaxx and Titan product lines, can also be accommodated including, but not limited to:

| SonoSite Probe | Major Uses |
| --- | --- |
| C11/8-5 | pediatric and neonatal abdomen, pediatric cardiac, pediatric head, vascular access, nerves |
| C60e | Abdominal, obstetrics, gynecology |
| P10/8-5 | Cardiac, neonatal heads, abdomen and vascular |
| P17/5-1 | Cardiac, abdominal, obstetrics |
| L25/10-5 | facilitating needle guidance in vascular access procedures |
| L38e | Small parts, breast, vascular, nerve, IMT, musculoskeletal, superficial |
| HFL38 | Breast, small parts, nerve, vascular, IMT, musculoskeletal |

The probe holder of this embodiment can also be adapted to hold ultrasound probes manufactured by Philips Medical (Bothell, Wash.), GE Medical (Waukesha, Wis.), Siemens Medical (Malvern Pa. and Mountain View, Calif.), Terason (Burlington, Mass.), Bard Access Systems (Murray Hill, N.J.), Tera Recon (San Mateo, Calif.) and Zonare (Mountain View, Calif.), among many others. The probe holder is not limited to mounting of ultrasound probes, but can be adapted to grip and hold a variety of imaging devices, as well as other tools that may benefit from arm-mounting and the flexibility of the probe holder.

Notably, as the size (thickness) of a probe increases, typically its weight also increases. This increased weight impacts the effectiveness of the fine adjust mechanism as a heavier probe may be so heavy that its weight overcomes the friction of the ball joint supporting it causing the probe to creep or fall away from its intended position. The design of the illustrative probe holder 500 specifically addresses this issue by exerting more pressure on the fine adjust ball joint 514 when larger and heavier probes are inserted. This increases the joints holding friction proportionally.

Figure 7:
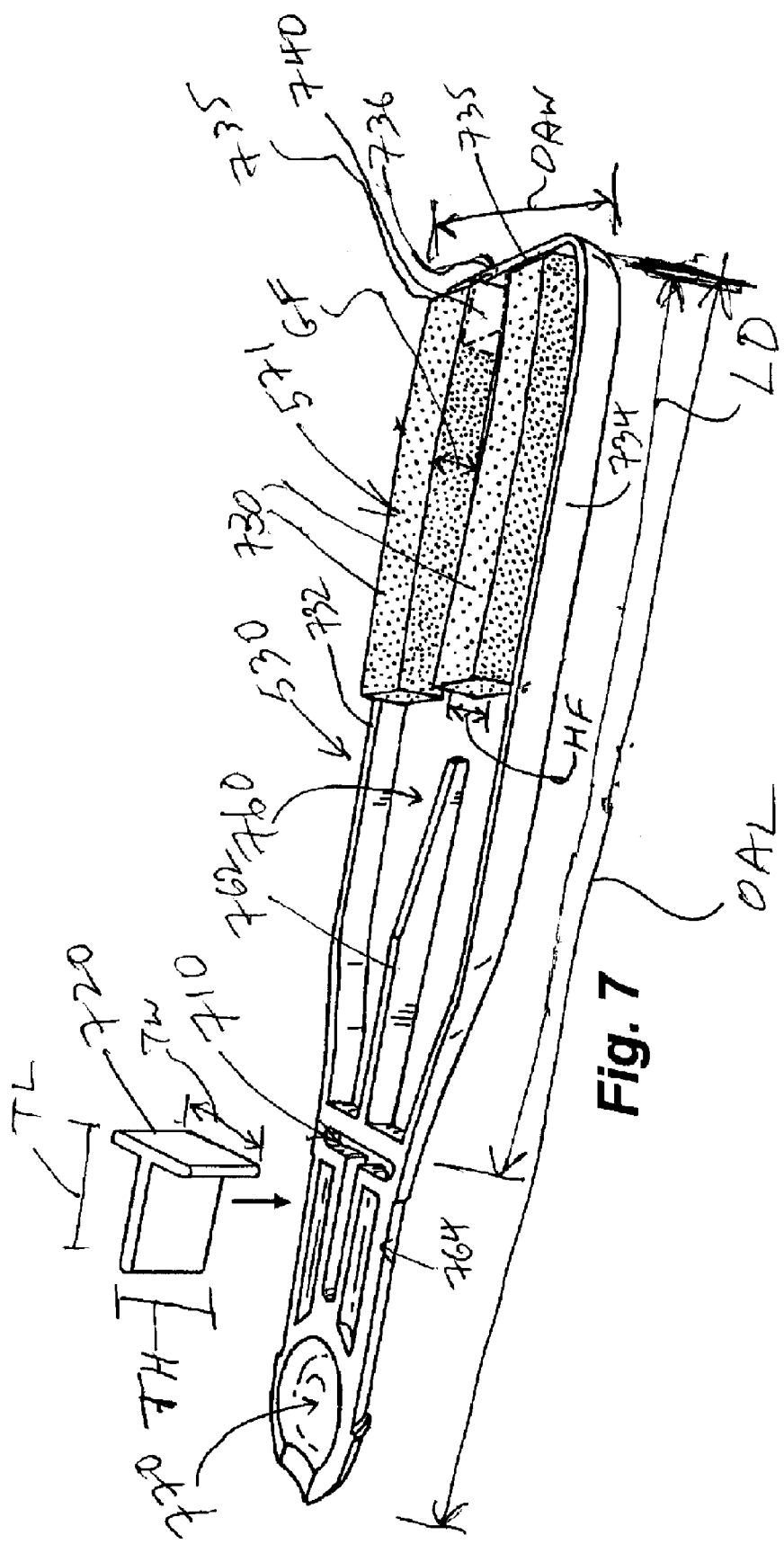
FIG. 7 is an exploded perspective view of a side of the probe holder and T-shaped fulcrum.

The internal construction of a clamp plate 530 is shown in further detail in FIG. 7. In this embodiment, each plate 530 has an overall width OAW of approximately 30-60 millimeters. The length LD of the probe-gripping distal portion (forward of a T-slot 710 described further below) is between approximately 100 millimeters and 160 millimeters. The Overall length OAL of the clamp plate 530 is approximately 150-200 millimeters. The diameter DB of the base member's ball 514 (see FIG. 6) is between 15 and 25 millimeters. These measurements are highly variable, and, in part dependent on the weight and size of the typical probe or other item to be grasped.

Grasping is accomplished by an elastomeric pad 571 that can be formed with a variety of surface contours, depending, in part, upon the geometry of the item to be grasped. A generalized shape is shown consisting of two separate pads 730 disposed against opposing widthwise side edges 732, 734 adjacent to the plate's distal edge 736. The distal tips 735 of each pad are rounded-over in this embodiment to facilitate insertion of a probe or other item as described below. The widthwise separation between pads 730 allows the overall structure to give way under pressure and cradle the bulged center of a typical probe. An optional distal pad 740 (shown in phantom) can be provided against the plate's distal edge 736 in an alternate embodiment to apply further frictional holding force to grasped item. In this example, each pad 730 has an approximate height HF of between 3 and 8 millimeters. The spacing between pads GF is approximately 15-10 millimeters. These dimensions are exemplary, and highly variable.

The interior of each clamp plate 530 defines, on its distal, clamping side, a shallow dish with the side edges 732, 734 and distal edge 736 being raised off the inner face 760 to define a well that is a few millimeters (3-5 millimeters, for example) deep. The well, lightens the overall structure, while allowing the pads 730 to resist detachment due to sliding. The well also makes for easier assembly and alignment of pads 730. The side edges and distal edge 732, 734, 736 provide requisite beam strength and rigidity to the plate 530. Additional strength can be provided by a proximally directed central stiffening rib 762 that has a distal ramp, and can help to establish a rear stop for a grasped probe.

The thickened area 764 containing the T-slot 710 forms the proximal wall of the well. The T-slot 710 receives a molded T-shaped member. It has a height TH of approximately 30-35 millimeters, a width TW of approximately 20-25 millimeters and a length TL of approximately 20-25 millimeters. These dimensions are highly variable in alternate embodiments. The T-shaped member establishes a rear backstop for proximal movement of the probe. It also provides an alignment guide in the widthwise and proximal-to-distal directions, preventing the two confronting clamp plates 530 from separating due to sliding apart. A variety of attached and/or unitary alignment guides can be employed according to alternate embodiments. The T-shaped member 720 is sized relative to each slot 710 so as to limit movement of the clamp plates 530 toward each other when not grasping a probe. Thus, the T-shaped member establishes a minimum spacing between the clamp plates.

The proximal end of the thickened area 764 contains a hemispherical well 770. This well is sized to conform to the outer diameter of the ball 514 on the base 512. The ball 514 and/or the well can be smooth or contain a textured surface to vary the fictional properties when the ball and wells of each clamp plate 530 are pressurably engaged.

Each clamp plate 530, T-shaped member 720 and base 512 can be molded, cast or machined as appropriate from a composite, polymer or metal. Some exemplary materials include, but are not limited to, ABS, Acetyl Copolymer, Delrin, polyethylene terephthalate—polyester, Noryl, Nylon, Polycarbonate, UHMWPE, Radel A (Polyethersulfone), RADEL® R (Polyphenylsulfone) (other PPSs like Ryton), Techtron (PolyPhenylene Sulfide), Ultem (PolyEtherImide), glass-filled nylon, glass-filled epoxy, aluminum alloy, and/or magnesium alloy.

Figure 8:
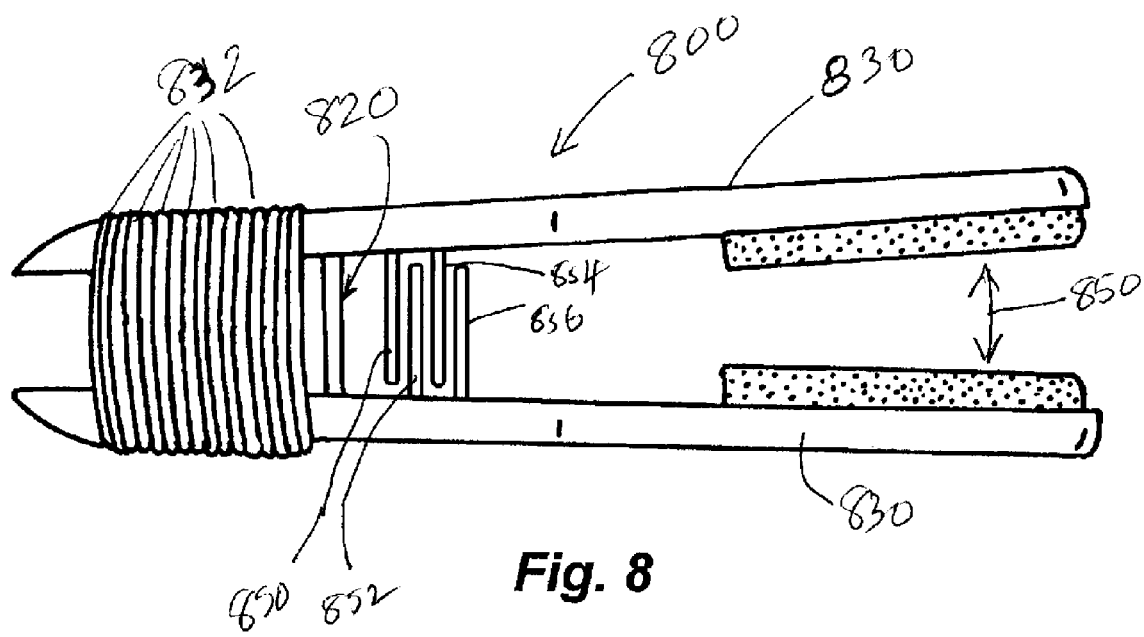
FIG. 8 is a side view of a probe holder including alignment members according to an alternate embodiment.

FIG. 8 details a probe holder 800 according to an alternate embodiment, showing an assembled pair of clamp plates 830 connected by one or more elastic bands 832, as described above. In this embodiment alignment is achieved by vanes 850, 852, 854 and 856 are provided in pairs (850, 854) and (852, 856). These vanes are formed unitarily with each plate in this embodiment. In general, alignment vanes are defied as unitary members that extend in an overlapping relationship, as shown, so as to prevent excessive skew between the joined plated, but to allow movement (double arrow 850) of the plates 830 toward and away from each other. The vanes can include hooks, nubs, interengaging tracks or other protuberances that capture the movement of the plates and limit the movement to predetermined maximum and/or minimum values. For example, the vanes can include J-shaped extensions at their widthwise edges that engage each other, and limit side-to-side (widthwise) movement. These alignment vanes can also be constructed or molded to lie axially along the length of the paddle to better restrict widthwise movement in an illustrative embodiment. Both types of veins and combinations of unitarily attached veins are expressly contemplated as "unitary alignment members."

Figure 9:
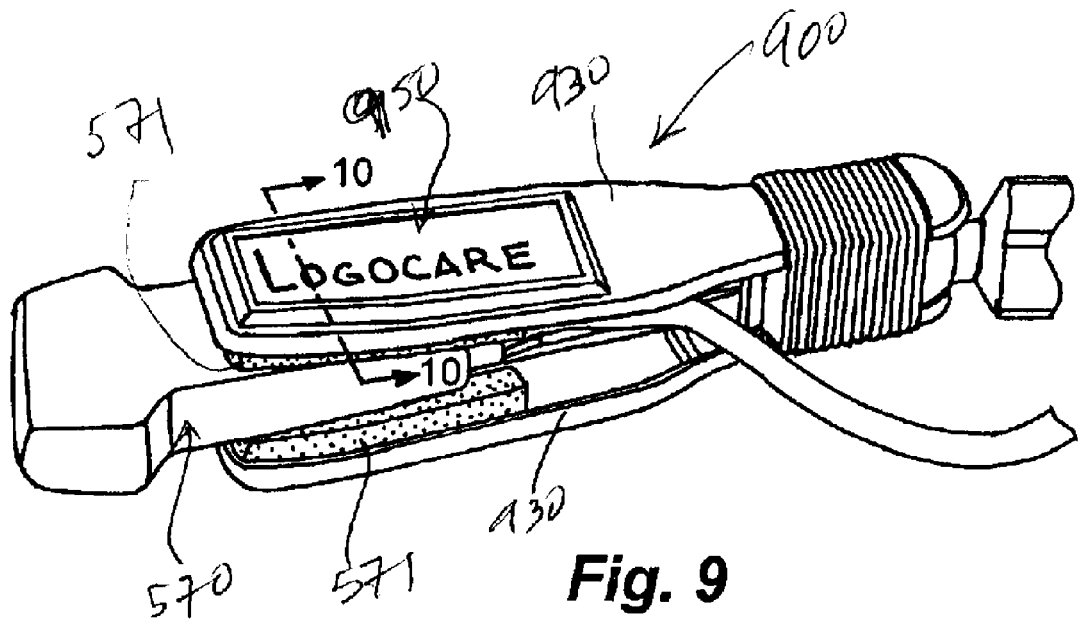
FIG. 9 is a perspective view of the probe holder according to an embodiment of this invention, including a grip with printed logo.
Figure 10:
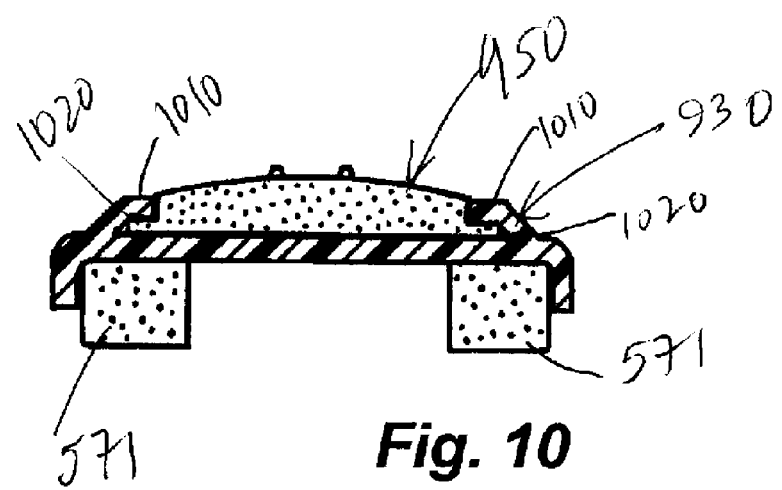
FIG. 10 is a front cross section taken along line 10-10 of FIG. 9.

FIGS. 9 and 10 detail an optional addition to a probe holder 900, which is otherwise similar to that of FIG. 5. The plates 930 include optional exterior gripping surfaces 950. The gripping surface 950 is constructed from any acceptable material that affords a non-skid surface to the probe holder. For example, silicone or various rubbers can be employed. The gripping surface can be contoured to afford an enhanced ergonomic surface for the practitioner's hand. Moreover, the gripping surface 950 can include an embossed, debossed, printed or molded-in logo (or other information/decoration). As shown in FIG. 10, the top surface of the clamp plate 930 can include ledge or undercut 1010 that captures a flange or outward wedge 1020 the base of the gripping surface. This arrangement allows for easy change-out of the gripping surfaces with others. Notably, gripping surfaces with differing decorations/logos or differing ergonomic features can be easily switched at the manufacturer's or end-user's location. These flanges may also serve as strengthening ribs, adding structural support to the clamp plates. Alternatively, a logo plate may be snapped into place over the clamp plate edges 732, 734, 736, thus permitting plain plates to use the same mold or machinist design as their contoured and logoed counterparts.

Figure 11:
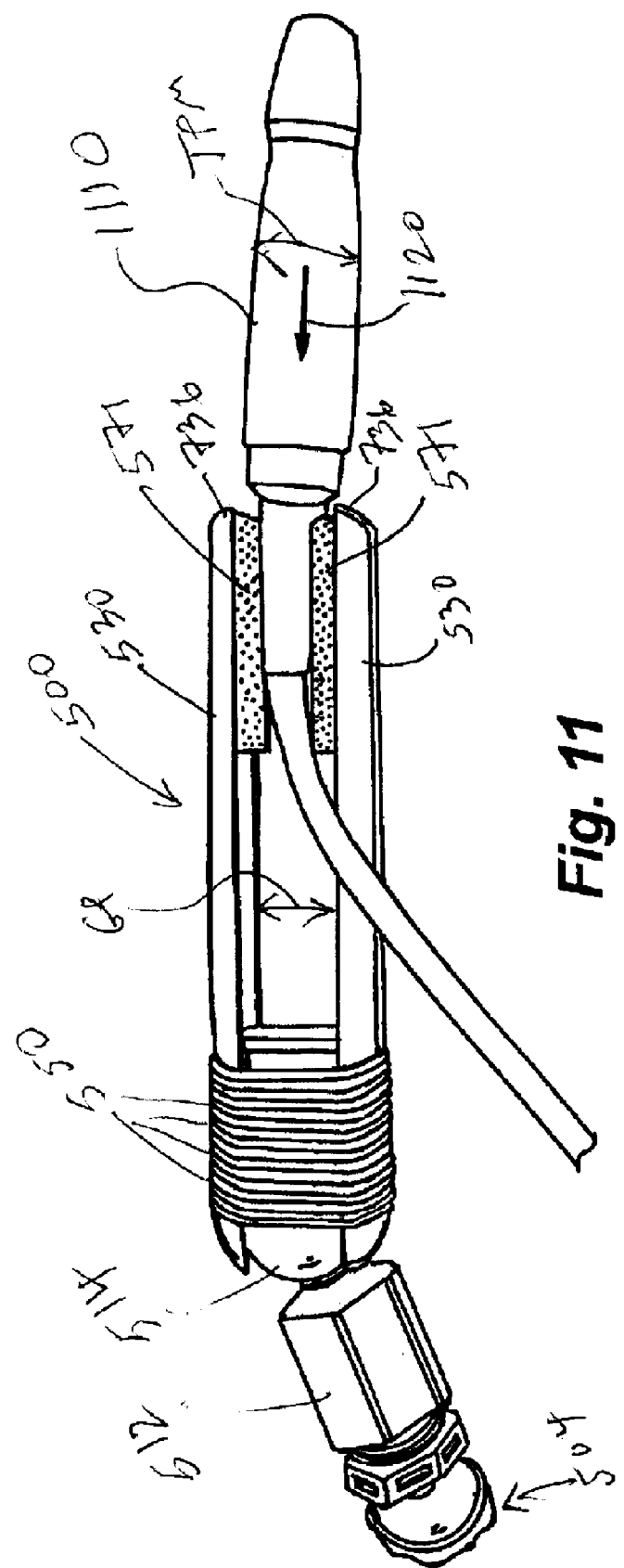
FIG. 11 is a side view showing the insertion of a first sized probe into the holder.
Figure 12:
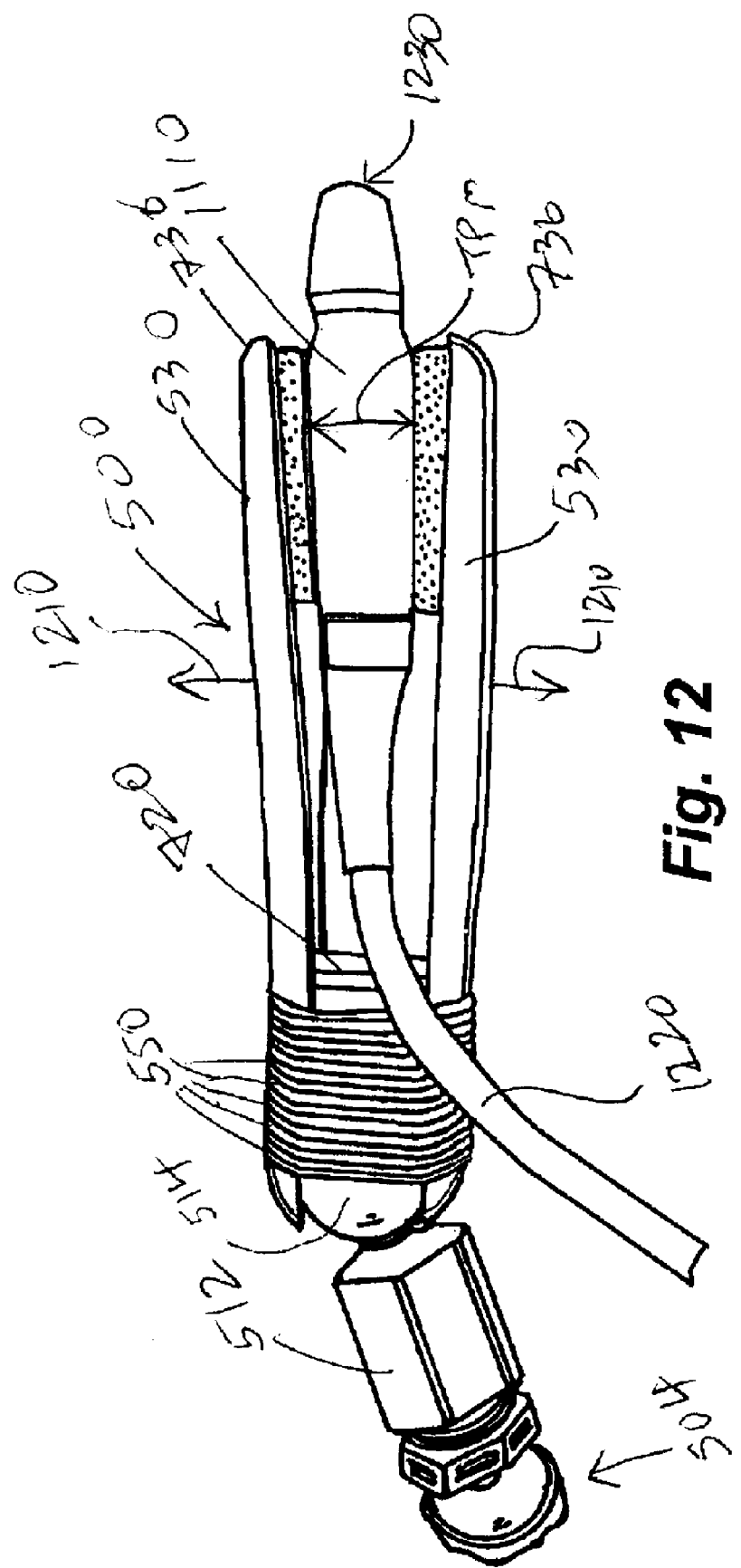
FIG. 12 is a side view showing the completed insertion and engagement of the probe within the holder of FIG. 11.
Figure 13:
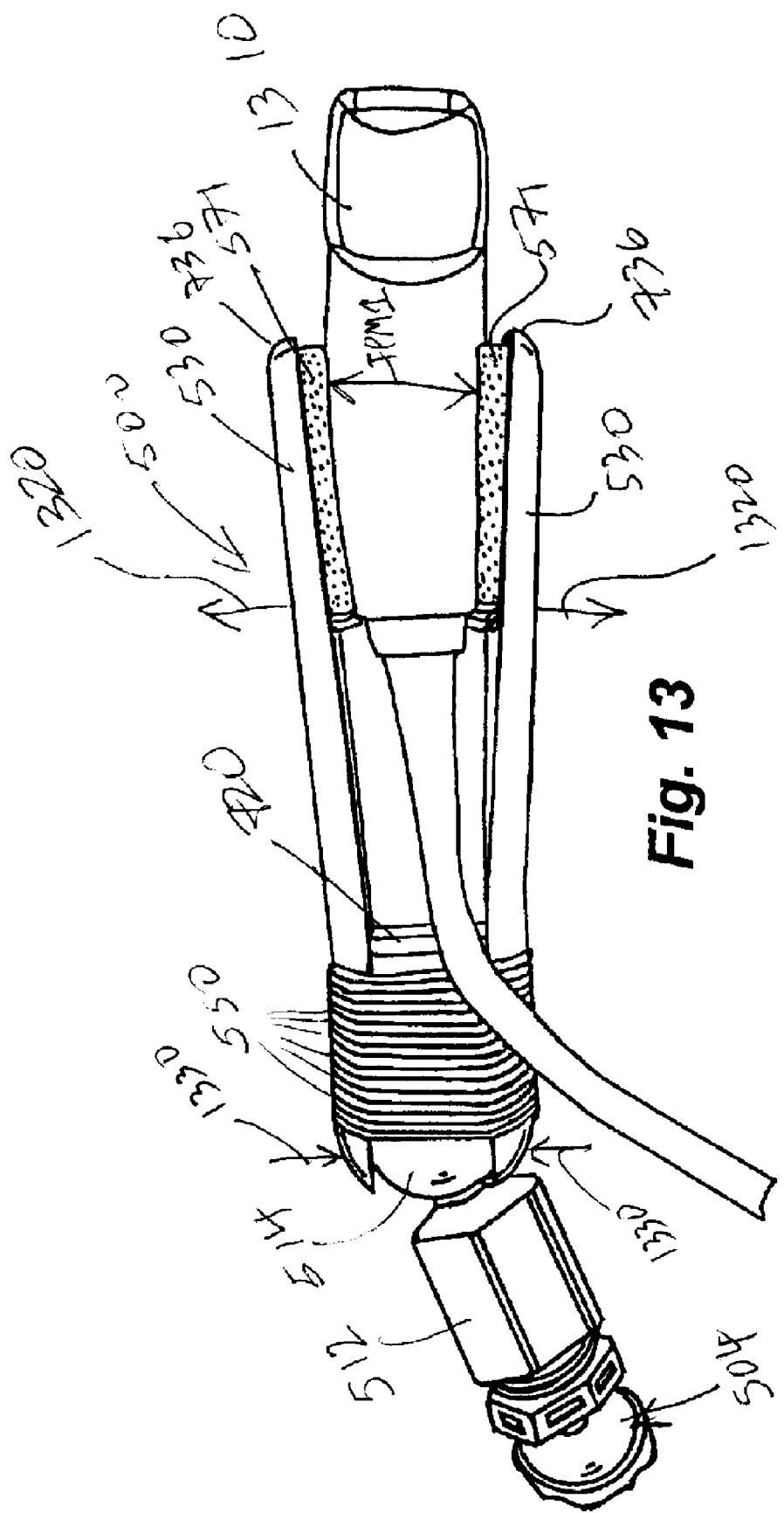
FIG. 13 is a side view showing the completed insertion of a second, larger-sized probe into the holder.

FIGS. 11-13 detail the insertion of probes of differing sizes into the jaws of the probe holder 500 according to the embodiment of FIG. 5. The clamp plates 530 are biased by the bands 550 into a minimum gap GP that is between approximately 10 to 20 millimeters. The probe 1110, having a first maximum thickness TPM, is biased (arrow 1120) proximally toward the distal edges 736 of the plates 530. The pads 571 are spaced so as to be closer together than the smallest thickness of a probe or other item to be gripped. The above-described rounded-distal edges of the pads 571 aid in receiving the probe 1110 and allowing the plates to spread as the probe is inserted proximally thereinto.

With reference to FIG. 12, the probe 1110 has been moved proximally into full engagement with the pads 571. The resistance of the bands 550 is overcome to allow the plates 530 to spread (arrows 1210), rotating around the ball 514. The probe head 1230 is exposed sufficiently beyond the plates' distal edges 736 to allow it to engage the target area without interference from the probe holder 500. It should be noted that the general construction of the probe holder, with minimal moving parts and reinforced, low-profile plates ensures that the holder does not add bulky appurtenance to an otherwise ergonomic probe. Rather, the probe holder 500 affords an additional grip layer to the probe that remains within the ergonomic limits desired by a practitioner.

In the fully gripped orientation of FIG. 12, the probe cable 1220 extends from the open side of the plate pair. The cable 1220 can be chased to the imaging device (not shown) in a variety of ways, including an internal chase that extends through the center of the arm 504. Note that the pads 571 are compressed by the force of the bands 550 to comply with the curvilinear surface profile of the probe 1110.

As shown in FIG. 13, a larger probe, having a maximum thickness TPM1, is gripped by the plates 530. The plates are further expanded (arrows 1320) relative to FIG. 12. In an illustrative embodiment a maximum expansion of between approximately 30-40 millimeters at the distal edges 736 is provided.

As discussed above, the design of this invention allows for a variety of sizes and weights of probes/items. As the distal end is expanded, the compression applied by the plates' proximal ends at the ball 514 increases (arrows 1330). This compression increases the relative force on the ball 514 by the clamping plates 530, which increases the holding force therebetween. This increased holding force generally compensates for the increased weight of larger probes.

Advantageously, the design of the probe holder enables one-handed insertion of the probe into the jaws of the holder via the distal end or through the side edges. The practitioner grasps the holder, while also handling the probe as it is aligned with the open space between plates. The holder and probe are squeezed together so that the probe forces the plates to spread apart. Eventually the squeezing places the probe in the desired clamped position with respect to the holder.

Figure 14:
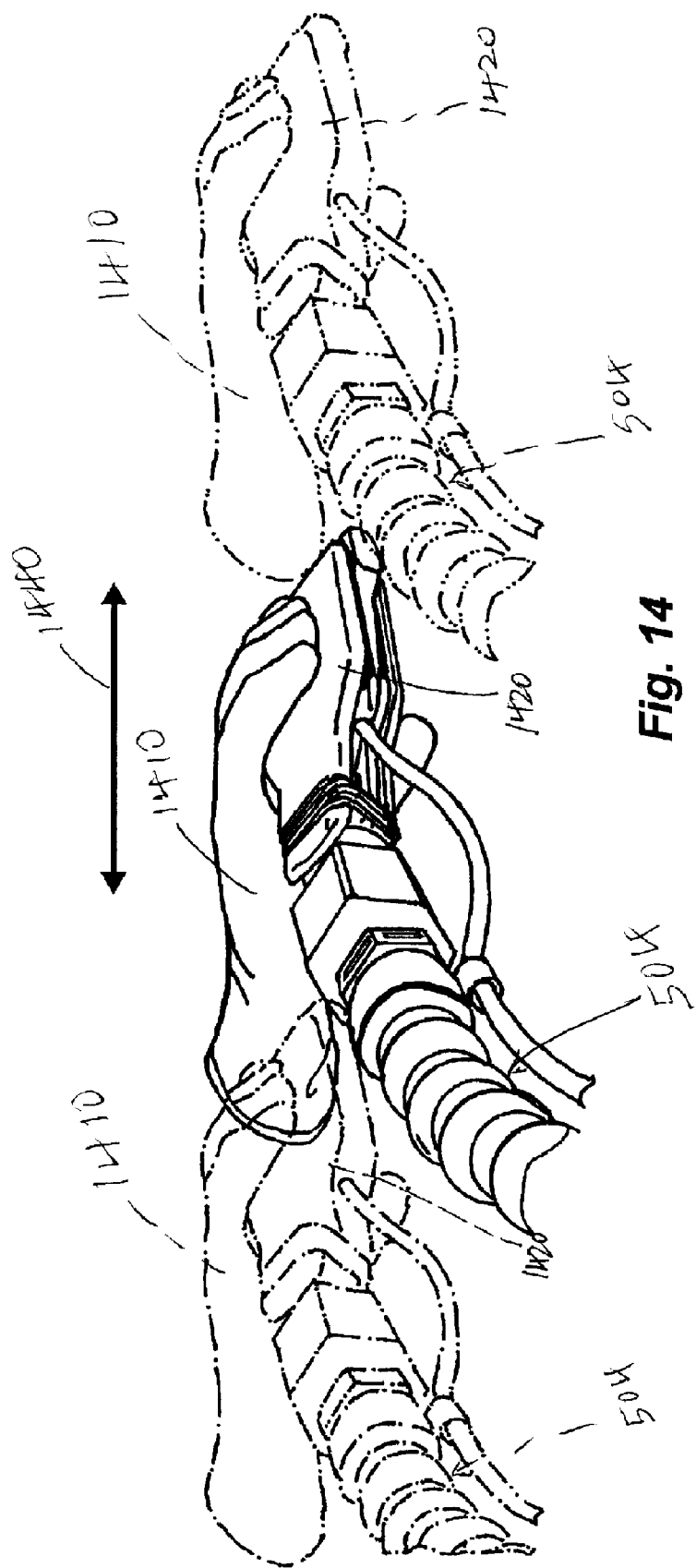
FIG. 14 is a perspective view of manipulation of probe alignment employing an arm-mounted probe holder in accordance with an illustrative embodiment.

The ball-and-well interengagement between the base 512 and the plates 530 affords a swivel joint that can be moved in three degrees of freedom relatively readily, but still tends to hold its position once placed on a target area. The desired ability to effect alignment, rotation and tilt are therefore satisfied. In FIG. 14, alignment with the target area in one or two orthogonal axes is achieved when the practitioner's hand 1410 grasps the probe holder 1420 and forces the entire flexible arm 504 along a relatively linear vector (arrow 1440). The segments articulate with respect to each other to allow the probe to move to its desired alignment in one or two orthogonal axes. The ball joint of the holder 1420 allows the desired attitude and rotation of the holder/probe to be maintained with minimal applied force as the gross alignment is applied.

Having achieved gross alignment with the target area, the practitioner's hand 1410 can now rotate the probe holder (curved arrow 1510) about a central axis 1520 to achieve the desired probe head orientation with respect to the target area. This desired rotation can depend upon the image viewed at the display. Rotation largely involves fine adjustment in which the plates rotate about the ball, with minimal arm segment articulation.

Figure 15:
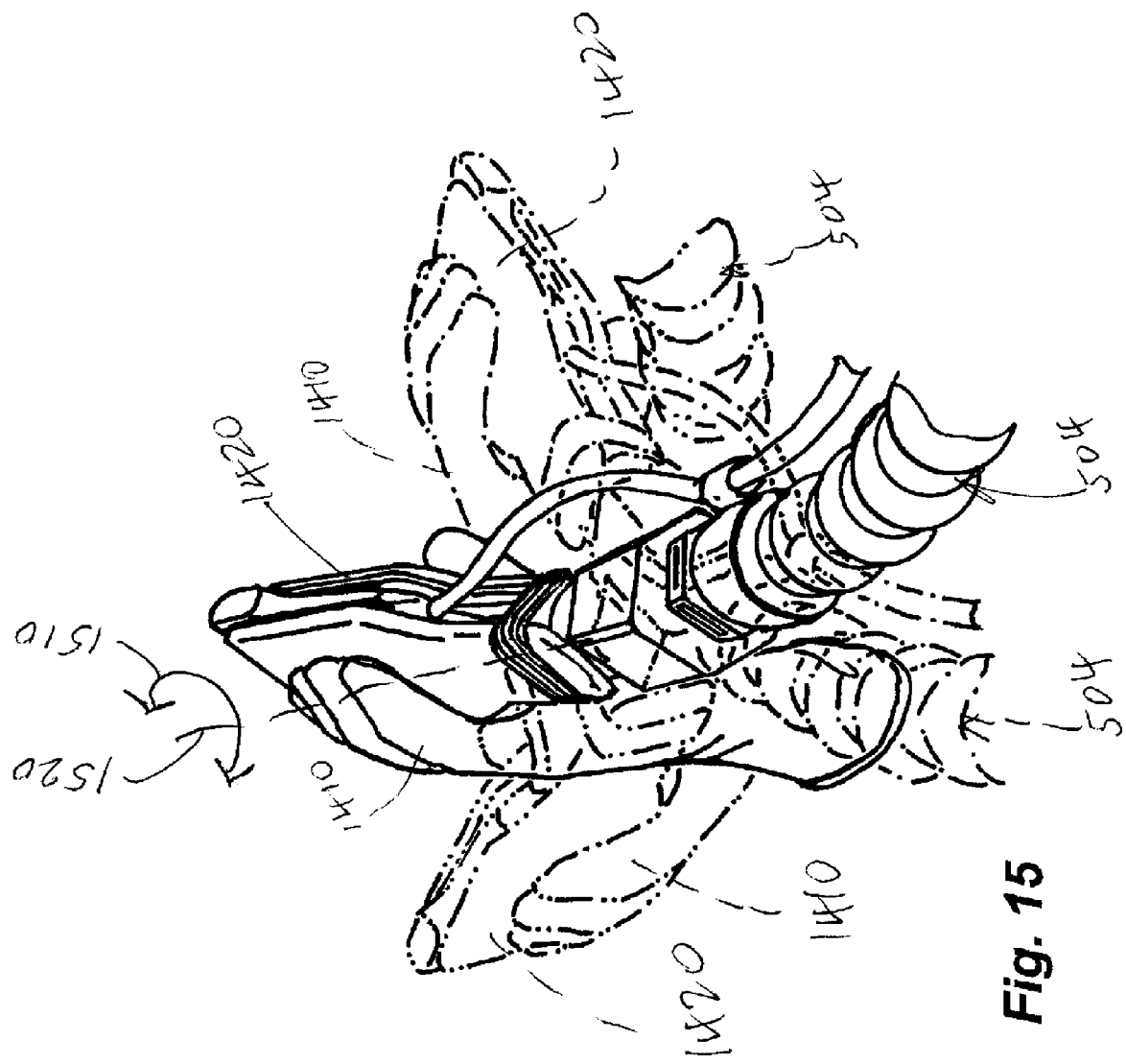
FIG. 15 is a perspective view of manipulation of probe rotation employing an arm-mounted probe holder in accordance with an illustrative embodiment.
Figure 16:
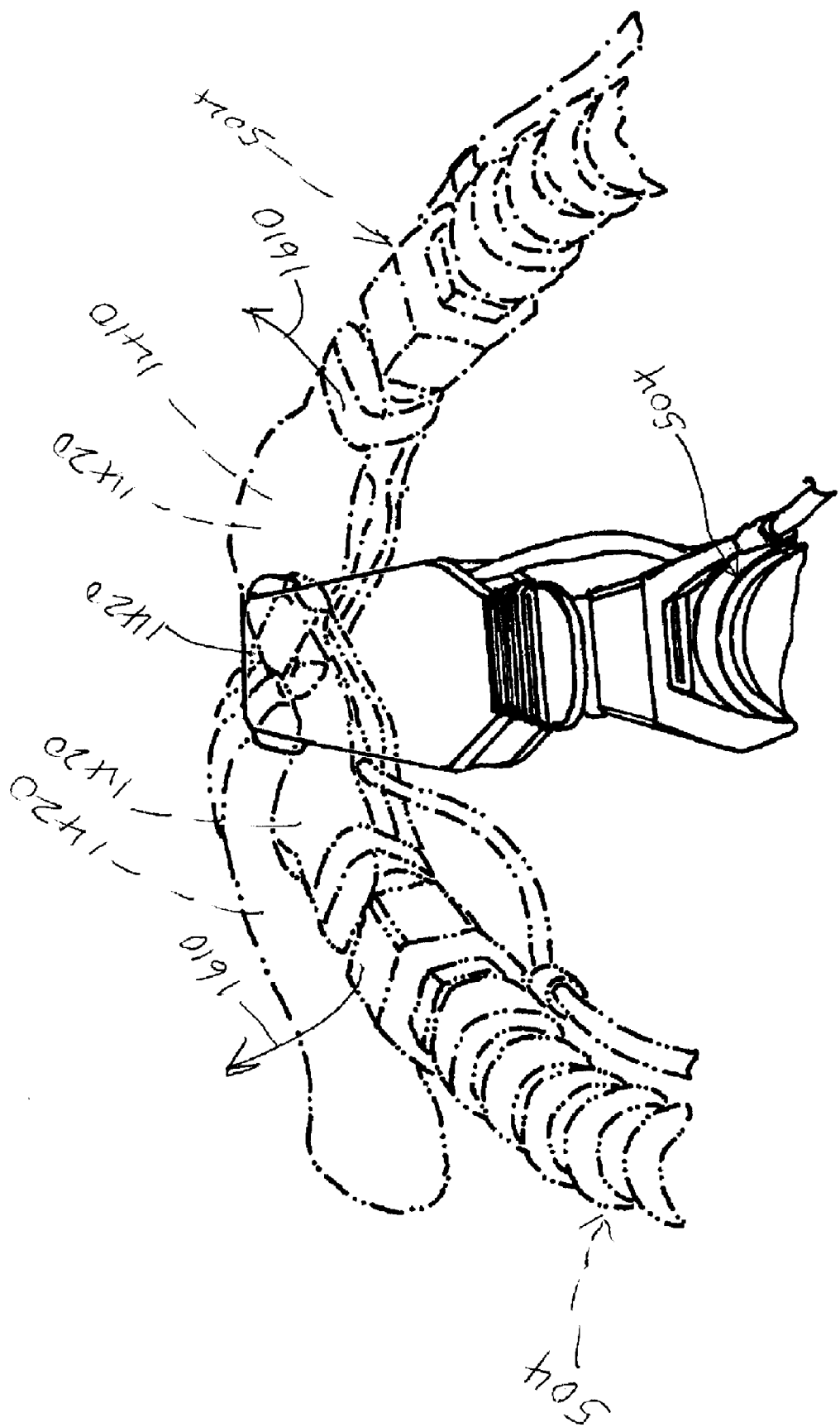
FIG. 16 is a perspective view of manipulation of probe tilt employing an arm-mounted probe holder in accordance with an illustrative embodiment.

Before or after rotation (FIG. 15), the practitioner may need to tilt the probe head to acquire the best engagement with the target surface (e.g. create a face-to-face contact between a curved body part and the probe head). FIG. 16 shows a tilting move by the practitioner's hand 1410 in which the probe holder 1420 is tilted (arrows 1610) to change the relative angle of the probe, against a surface, while maintaining alignment and rotation. Alternatively, the practitioner may tilt the probe relative to the surface along an axis that is parallel to the probe's viewing area. The ball joint enables relatively easy tilt at the joint. Some degree of force is imparted to bias the segments of the arm 504 into the new tilt attitude. However, the leverage that the tilting action exerts on the segments assists in easing the force required to articulate the segments during tilt.

Note that, in practice, alignment, rotation and tilt can occur simultaneously or in various combinations.

Figure 17:
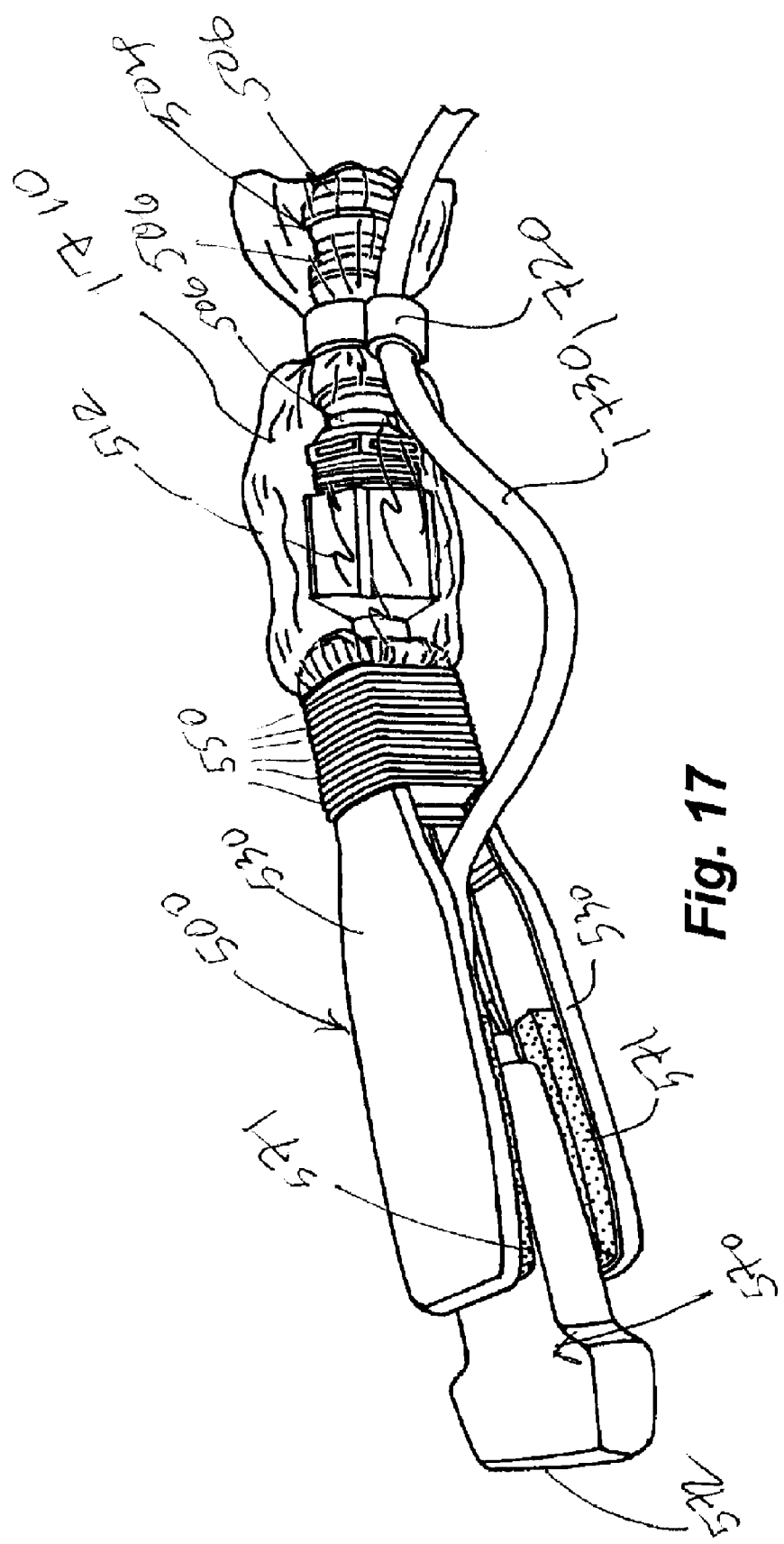
FIG. 17 is a perspective view of the probe holder and attached flexible arm including a novel transparent cover and wire clip assembly in accordance with an embodiment of this invention.

An additional feature that has both a decorative and hygienic purpose is shown in FIG. 17. Typically, the arm 504 is covered in a cover during use. The arm segments 506 can be provided in one or more pleasing colors. For example, in a pediatric environment it may be desirable to provide a multicolored set of segments (adjacent segments each having distinct colors), along with a colorful probe holder. The arm segments can be exposed, while still maintaining a smooth, gapless exterior by providing a tubular, transparent cover 1710. The cover can be colored or tinted in certain embodiments and/or can contain patterns, decorations or wording printed thereon. The distal end of the cover is tucked under the bands 550 in this embodiment, creating a sealed surface from the holder to a selected proximal location (not shown). The location of distal termination of the cover is highly variable. Special bands or seals can be employed to attach the distal end of the cover at any location along the probe holder or proximally thereof. Note that a clip 1720 is provided along the exterior of the cover 1710 to chase the probe cable 1230. The clip 1720 and cable 1730 can be positioned beneath the cover 1710 in alternate embodiments.

It should be clear that the above-described probe holder affords the user a highly flexible and finely tunable grip with which to maintain a probe head against a target area. This probe holder adapts to differing sized and weighted probes (and other items), and applies increased holding force to heavier probes so as to assist in maintaining their position. The probe holder maintains a relatively low profile, making it ergonomic.

The foregoing has been a detailed description of illustrative embodiments of this invention. Various modifications and additions can be made without departing from the spirit and scope thereof. For example, the bias mechanism can be any force-applying mechanism, including mechanical springs and associated spring linkages (hinges, etc.). The compression plates can be aligned, and held together against skew, in a variety of ways, using unitary or separate alignment components. The holder's base can be attached to the arm in a variety of ways, including, but not limited to, bayonet-style connectors, spring-loaded quick-disconnects, compression fitments, and the like. Moreover, the ball joint can include supplemental locking mechanisms, such as clamps, set screws, and the like. In addition, while an undercut-interference fit is described, the gripping surfaces can be applied to the exterior surfaces of the clamp plates using a variety of techniques including, but not limited to adhesives, friction fit, fasteners, static molding and plastic welding. Accordingly, this description is meant to be taken only by way of example, and not to otherwise limit the scope of the invention.

What is claimed is:

1. A holder for a medical imaging probe comprising:
   A base constructed and arranged to engage a distal end of a flexible arm, the base including a ball joint;
   A pair of confronting clamping plates, each having a distal end adapted to frictionally secure the medical imagining probe and proximal end having a hemispherical well sized to engage a ball end of the ball joint;
   An alignment member, which has a general T-shaped member, located distally of the well that movably aligns the confronting claiming plates; and
   An elastic band surrounding each of the clamping plates and located adjacent to the alignment member and the ball joint that biases the plates toward each other and toward the ball, the spring acting on the plates substantially distally of a diametral axis of the ball.

2. The holder as set forth in claim 1 wherein the plates each include a slot adjacent to the proximal end, the alignment member having opposing sides each respectively inserted into each slot.

3. The holder as set forth in claim 1 wherein flexible arm comprises a plurality of interengaged, polymer ball-and-socket segments.

4. The holder as set forth in claim 3 further comprising a transparent cover that extends from a location adjacent to the plates to predetermined proximal location along the arm.

5. The holder as set forth in claim 4 wherein a distal end of the cover is secured beneath the elastic band assembly.

6. The holder as set forth in claim 1 wherein an exterior surface of each of the plates includes a pliable gripping surface.

7. The holder as set forth in claim 4 wherein the plates include an undercut sized and arranged to receive a conforming structure on each respective gripping surface.

8. The holder as set forth in claim 7 wherein the gripping surface includes a decoration applied thereto.

9. The holder as set forth in claim 1 wherein the flexible arm comprises a plurality of interengaged, polymer ball-and-socket segments and further comprising a cable clip that secures a probe wire to one of the segments of the flexible arm.

10. The holder as set forth in claim 3, wherein the flexible arm further comprises a transparent cover that surrounds the plurality of interengaged, polymer ball-and-socket segments from a location adjacent to the distal end to a predetermined proximal end along the probe.

11. The holder as set forth in claim 10 wherein the segments comprise a plurality of discrete colors.

12. The holder as set forth in claim 10 further comprising a wire clamp that surrounds an exterior of the cover and that secures a cable of the imaging probe.

* * * * *